United States Patent [19]

Radmacher

[11] Patent Number: 5,342,515

[45] Date of Patent: Aug. 30, 1994

[54] CHROMATOGRAPHIC COLUMN

[75] Inventor: Edmund Radmacher, Duren, Fed. Rep. of Germany

[73] Assignee: Macherey, Nagel & Co., Duren, Fed. Rep. of Germany

[21] Appl. No.: 143,387

[22] Filed: Oct. 29, 1993

Related U.S. Application Data

[63] Continuation of Ser. No. 16,829, Feb. 12, 1993, abandoned.

[30] Foreign Application Priority Data

Feb. 14, 1992 [DE]  Fed. Rep. of Germany ... 9201885[U]

[51] Int. Cl.⁵ .............................................. B01D 15/08
[52] U.S. Cl. ................................. 210/198.2; 210/656; 96/104; 96/106
[58] Field of Search .......... 210/635, 656, 198.2, 210/238, 232; 422/70; 96/101, 106, 104

[56] References Cited

U.S. PATENT DOCUMENTS

| | | | |
|---|---|---|---|
| 3,904,527 | 9/1975 | Wilhelmson | 210/198.2 |
| 4,283,280 | 8/1981 | Brownlee | 210/198.2 |
| 4,313,828 | 2/1982 | Brownlee | 210/198.2 |
| 4,399,032 | 8/1983 | Mott | 210/198.2 |
| 4,451,364 | 3/1984 | Higgins | 210/198.2 |
| 4,478,715 | 10/1984 | Goodnight | 210/198.2 |
| 4,563,275 | 1/1986 | McEachern | 210/198.2 |
| 4,565,632 | 1/1986 | Hatch | 210/198.2 |
| 4,636,316 | 1/1987 | Harris | 210/198.2 |
| 4,655,917 | 4/1987 | Shackelford | 219/198.2 |
| 4,719,011 | 1/1988 | Shalon | 210/198.2 |
| 4,737,284 | 4/1988 | Hauke | 210/198.2 |
| 4,769,141 | 9/1988 | Couillard | 210/198.2 |
| 4,806,238 | 2/1989 | Sattler | 210/198.2 |
| 4,861,473 | 8/1989 | Shackelford | 210/198.2 |
| 4,876,005 | 10/1989 | America | 210/198.2 |

FOREIGN PATENT DOCUMENTS 205002  5/1986  European Pat. Off. ......... 210/198.2

OTHER PUBLICATIONS

Waters Steel Cartridge Column Care and Use, PN 036682 Rev., Apr. 1991, pp. 1-6.

*Primary Examiner*—Ernest G. Therkorn
*Attorney, Agent, or Firm*—Joseph W. Berenato, III

[57] ABSTRACT

This invention relates to a chromatographic column with a separation column which is equipped on at least one side with an end threading mechanism for connecting a capillary, a precolumn, or another separation column, whereby the end threading mechanism has a support nut surrounding the column tube and a coupling nut, and the support nut is supported towards the corresponding end of the separation column at a stop part which is held in a recess at the separation column wherein the column has several axially consecutive recesses.

8 Claims, 2 Drawing Sheets

CHROMATOGRAPHIC COLUMN

This is a continuation of application Ser. No. 08/016,829, filed on Feb. 12, 1993, now abandoned.

The invention relates to a chromatographic column with a separation column which is equipped on at least one side with an end threading mechanism for connecting a capillary, a precolumn or another separation column, whereby the end threading mechanism has a support nut surrounding the column tube and a coupling nut, and the support nut is supported towards the corresponding end of the separation column at a stop part which is held in a recess at the separation column.

Such a chromatographic column is sold by WATERS Chromatography Division of Millipore Corporation. Its separation column has on the end an annular groove into which a C-shaped clip may be inserted as a stop part, whereby the clip is shaped so that it performs a snap-in movement in the process. This clip functions as a stop for a support nut which is constructed as a cap nut and which is pushed onto the separation column prior to the insertion of the clip.

In order to connect the separation column with a capillary, the end threading mechanism has a coupling nut which has an exterior thread and which may be screwed with this thread into the interior thread of the support nut. The coupling nut is also constructed in cap-shape and in this way is able to press a transmitting piece onto the end of the separation column, whereby the end of a capillary can be screwed into the transmitting piece. In order to make the connection as tight as possible and have as little dead volume as possible, the separation column has frit and sealing elements set in at the ends.

A solution differing from the previously described chromatographic column is found in European Patent 0 205 002. The chromatographic column described there also has a separation column with an annular groove at the end, whereby the end threading mechanism also consists of a support nut and a coupling nut. The support nut here is however divided axially into two halves and has at the end an annular shoulder which projects inward and locks into the annular groove. This fixates the support nut axially when the coupling nut is screwed onto it.

In both previously known chromatographic columns the disadvantage exists that, in the case when instead of a capillary a precolumn or another separation column shall be connected, different sets of end threading mechanisms must be available so that this connection can be made. The invention therefore is based on the task of proposing a chromatographic column with an end threading mechanism of the initially mentioned type which, with the lowest possible number of parts, permits the connection of capillaries and precolumns even of different lengths, as well as additional separation columns.

According to the invention this task is solved in that the separation column has on at least one end several axially consecutive recesses, each of which accepts the stop part. This construction permits that the stop part can be fixed at the separation column at different distances from the frontal end of the separation column so that the support nut is supported in corresponding different positions in relation to the separation column. Hereby the distances of the recesses to the frontal end of the separation column are such that it is possible to connect a precolumn and/or different lengths of precolumns instead of a capillary using a single coupling nut. The number of recesses here has been matched to the number of different coupling possibilities. In the simplest case two recesses are sufficient. But it is also possible to provide three or even more recesses so that different types of precolumns can be connected.

It has been provided in the realization of the invention that the stop part is constructed in a manner known per se as a C-shaped clip. Hereby the clip and the recesses should be adapted to each other so that the clip performs a snap-in movement when inserted, i.e. it will be unable to fall out of the recess by itself.

The recesses are constructed as annular grooves, in a known manner. Although other types of recesses are conceivable, the annular groove was found to be a useful construction.

The coupling nut is constructed preferably as a cap nut so that it is possible to press in this way the capillary or the precolumn to be connected to the frontal end of the separation column. But it is also possible to construct the coupling nut as a coupling sleeve to connect two separation columns with support nuts which are directed against each other. This results in the possibility of realizing separation columns of varying lengths.

According to another characteristic of the invention it is provided that a low-dead-volume intermediate part which has projections for locking into the separation column and into another successive element, such as a precolumn or another separation column, is set onto the open end of the separation column. Hereby the projections should be constructed in truncated cone shape in order to achieve a good seal.

BRIEF DESCRIPTION OF THE DRAWINGS

The invention is illustrated in more detail in the drawing, using embodiments.

FIG. (1) shows the view of an end of a separation column with end threading mechanism;

Figure 1:
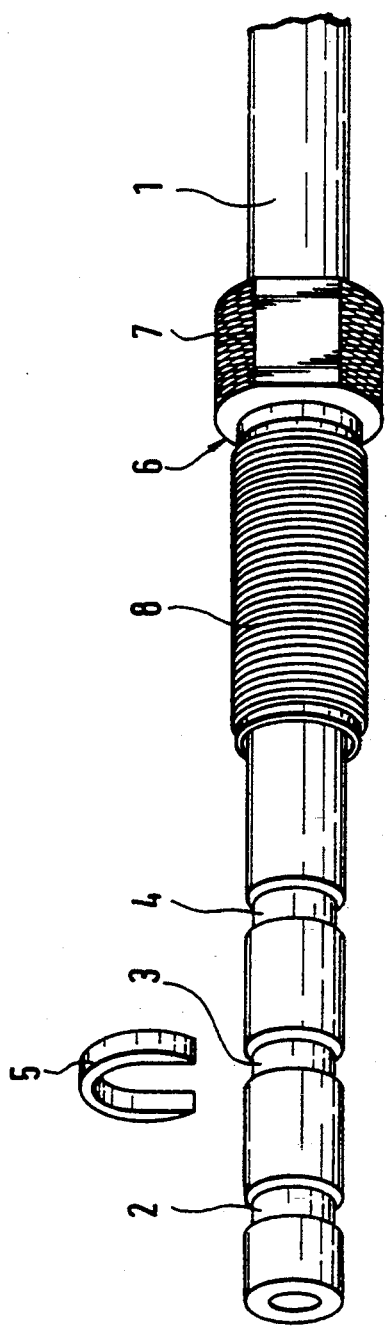
Figure 1:
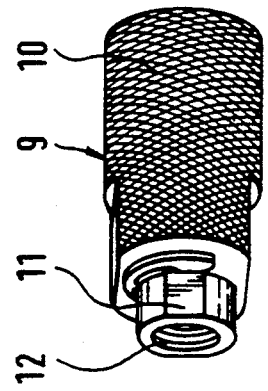
Figure 2A:
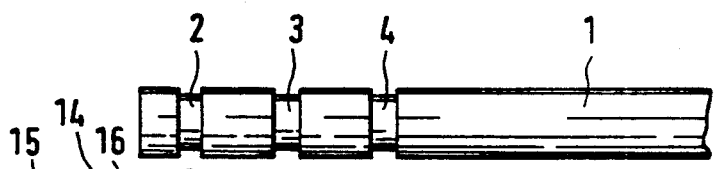
Figure 2B:
Figure 2C:
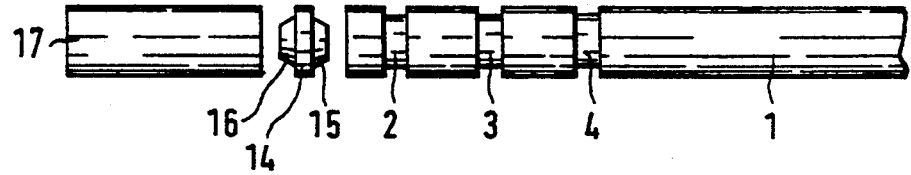
Figure 3:
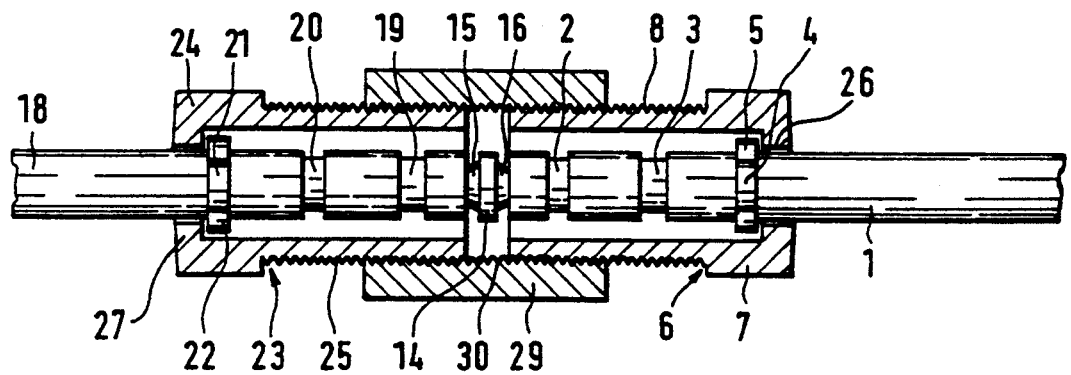

FIGS. (2a), (2b), (2c) show the lateral view of the end of a separation column without precolumn (a), with a small precolumn (b), and with a longer precolumn (c);

FIG. 3 shows a longitudinal section through the end threading mechanism for connecting two separation columns.

DESCRIPTION OF THE PREFERRED EMBODIMENTS

FIG. (1) shows the end part of a separation column (1) which is part of a chromatographic column. The separation column (1) is outfitted with a sorbent and is closed off at the end by a frit element and a seal which are not shown in detail here. The separation column (1) has towards the free end two annular grooves (2, 3, 4) which are at an axial distance from each other. A C-shaped clip (5) may be inserted from the side, i.e. in radial direction, into these annular grooves. The opening of the clip (5) hereby has such dimensions that the opening is first widened somewhat during insertion and then snaps closed somewhat again, so that the clip (5) is held captive in its end position. The clip (5) is thick enough that it projects in its end position beyond the exterior mantle of the separation column (1).

A support nut (6) which is constructed as a cap nut is pushed onto the separation column (1). It has a grip part (7) as well as an exterior thread part (8) which projects from the former towards the end of the separation column (1). The inside diameter of the support nut (6) is such that the support nut (6) can be pushed over the clip (5) until the support nut (5), with an annular shoulder which projects inward, comes to rest against the clip (5) at the side of the latter which is facing away from the end of the separation column (1). The clip (5) then prevents further movement of the support nut (6) in the direction towards the shown end of the separation column (1) and fixates it to that extent.

The axial extension of the separation column (1) shows a coupling nut (9) which is also constructed in cap-shape and has a grip part (10). It is constructed open towards the separation column (1) and has an interior thread which is not shown here and which is used to screw the coupling nut (9) onto the exterior thread part (8) of the support nut (6). Into the coupling nut (9) has been set a transmitting piece (11) which supports itself on an annular shoulder (not shown) of the coupling nut (9) which projects inward, so that the transmitting piece (11) can only be removed from the coupling nut (9) on the side facing towards the end of the separation column (1). When screwing the coupling nut (9) onto the exterior thread part (8) of the support nut (6), the transmitting piece (11) is pressed on the frontal side against the end of the separation column (1). Sealing elements which are not shown here ensure that the connection is sealed even under very high pressures.

The transmitting piece (11) has a through-hole (12) which is equipped with an interior thread into which the end of a capillary can be screwed in a sealing manner. The connection between a separation column (1) and a capillary therefore may be made by screwing together the support nut and the coupling nut (9).

FIG. (2) schematically shows various forms of connections without showing the end threading mechanism. FIG. (2a) shows the separation column (1) alone, i.e. without any precolumn. In this form, it is intended that the separation column (1) will be connected to a capillary, as described for FIG. (1). The clip (5) is then inserted into the annular groove (4), which has the farthest distance from the frontal end of the separation column (1).

FIG. (2b) shows the connection of a small precolumn (13). In this case, the clip (5) is inserted into the center annular groove (3), whereby the distance between the right annular groove (4) and center annular groove (3) is such that it is possible to use the same coupling nut (9) as shown in FIG. (1) to connect the small precolumn, since the support nut (6) is supported at a corresponding length closer to the end of the separation column (1).

Between the frontal ends of the separation column (1) and the small precolumn (13), a disc-shaped intermediate part (14), with bilateral projections (15, 16) which have a truncated cone shape, has been provided. The dimensions of the projections are such that the projections lock into the frontal openings of the separation column (1) on one side and of the small precolumn (13) on the other side. The intermediate piece (14) has a passage with the lowest possible dead volume for the medium to be analyzed.

FIG. (2c) shows the connection of a large precolumn (17)—again with interposition of the intermediate part (14). In this case, the clip (5) is inserted into the left annular groove (2) which is closest to the end of the separation column (1). The distance of this annular groove (2) to the right annular groove (4) is again such that the support nut is supported so close to the end of the separation column (1) that the same coupling nut (9) as was used also in the cases shown in FIG. (a) and (2b) can be used for pressing the large precolumn (17) onto the intermediate piece (14) or the separation column (1). Therefore, in all three cases it is not necessary to use parts other than the existing parts of the end threading mechanism. The same end threading mechanism can be used both for connecting a capillary and connecting precolumns with two different lengths.

FIG. (3) shows the connection of the separation column (1) to another separation column (18). The separation column (18) also has in its end part three annular grooves (19, 20, 21), and is constructed like separation column (1) to this extent. Its length may correspond to that of separation column (1), but may also be different.

Clips (5, 22) of the type described above are inserted into the annular grooves (4, 21) which are located at the respectively farthest distance from the ends. Support nuts (6, 23) which are directed against each other and are constructed identically and which previously had been pushed onto the separation columns (1, 18) rest against them. The support nuts have grip parts (7, 24) and exterior thread parts (8, 25), whereby the latter are adjoining each other. At their outside ends, they have inwardly projecting annular shoulders (26, 27) which support the support nuts (6, 23) at the clips (5, 22). The opposite ends of the support nuts (6, 23) end approximately flush with the frontal ends of the separation columns (1, 18). The low-dead-volume intermediate piece (14) which already was described earlier is again arranged between the two separation columns (1, 18).

In order that the separation columns (1, 18) are pressed against each other, a coupling sleeve (29), which for this purpose is equipped with an interior thread (30), is screwed onto the exterior thread parts (8, 25). The interior thread (30) is matched to the threads on the exterior thread parts (8, 23) in such a way that the support nuts (6, 23) are moved towards each other, so that they drive against each other, when the coupling sleeve (29) is turned in one of the two directions, and then exert a corresponding pressure when the separation columns (1, 18) rest against the intermediate piece (14). To release the connection, the coupling sleeve (29) is then turned in the opposite direction so that the support nuts (6, 23) are moved apart from each other.

I claim:

1. Chromatographic column with a separation column which is equipped on at least one side with an end threading mechanism for connecting a capillary, a precolumn or another separation column, whereby the end threading mechanism has a support nut surrounding the column tube and a coupling nut, and the support nut is supported towards the corresponding end of the separation column at a stop part which is held in a recess at the separation column,
    characterized in that the separation column (1, 18) has on at least one end several axially consecutive recesses (2, 3, 4, 19, 20, 21), each of which accepts the stop part (5, 22).
2. Chromatographic column according to claim (1), characterized in that the stop part is constructed as a C-shaped clip (5, 22).
3. Chromatographic column according to claim (2), characterized in that the clip (5, 22) and the recesses (2, 3, 4, 19, 20, 21) are adapted to each other so that the clip (5, 22) performs a snap-in movement when inserted into one of the recesses (2, 3, 4, 19, 20, 21).
4. Chromatographic column according to claim 1, characterized in that the recesses are constructed as annular grooves (2, 3, 4, 19, 20, 21).

5. Chromatographic column according to claim 1, characterized in that the coupling nut (9) is constructed as a cap nut.

6. Chromatographic column according to claim 1, characterized in that the coupling nut (29) is constructed as a coupling sleeve (29) for connecting two separation columns (1, 18) with support nuts (6, 23) which are directed against each other.

7. Chromatographic column according to claim 1, characterized in that a low-dead-volume intermediate part (14) which has projections (15, 16) for locking into the separation column (1, 18) and into another successive element (13, 17, 18) is set onto the open end of the separation column (1, 18).

8. Chromatographic column according to claim (7), characterized in that the projections (15, 16) are constructed in truncated cone shape.

* * * * *